United States Patent
Husk

(10) Patent No.: US 10,531,889 B2
(45) Date of Patent: Jan. 14, 2020

(54) SCISSOR MOUNTED BLOOD SPRAY SHIELD

(71) Applicant: Rod Husk, Cincinnati, OH (US)

(72) Inventor: Rod Husk, Cincinnati, OH (US)

( * ) Notice: Subject to any disclaimer, the term of this patent is extended or adjusted under 35 U.S.C. 154(b) by 335 days.

(21) Appl. No.: 14/923,750

(22) Filed: Oct. 27, 2015

(65) Prior Publication Data

US 2016/0128780 A1 May 12, 2016

Related U.S. Application Data

(60) Provisional application No. 62/069,886, filed on Oct. 29, 2014.

(51) Int. Cl.
| A61B 17/32 | (2006.01) |
| A61B 17/3201 | (2006.01) |
| A61B 90/00 | (2016.01) |

(52) U.S. Cl.
CPC .......... *A61B 17/3201* (2013.01); *A61B 90/05* (2016.02)

(58) Field of Classification Search
CPC ..... A61B 19/42; A61B 17/3201; A61B 90/05; A61B 17/42
USPC ......... 30/223, 173, 258, 134, 280, 232, 124, 30/136, 233; 128/746, 845, 849–856, 128/897; 606/1, 170, 119, 120, 174, 172, 606/167, 205–210; D8/57; D24/231
See application file for complete search history.

(56) References Cited

U.S. PATENT DOCUMENTS

| 731,687 | A |   | 6/1903 | Kanter |
| 1,600,225 | A | * | 9/1926 | Halpern ............. A61B 17/3201 30/233 |
| 2,234,472 | A |   | 3/1941 | Freel |
| 2,521,027 | A | * | 9/1950 | Sorensen ............... A45D 29/02 132/73 |
| 2,711,584 | A | * | 6/1955 | Crider .................... H02G 1/005 30/124 |
| 3,877,145 | A |   | 4/1975 | Andrews |
| 4,870,965 | A |   | 10/1989 | Jahanger |
| 4,949,734 | A |   | 8/1990 | Bernstein |
| 5,127,915 | A |   | 7/1992 | Mattson |
| 5,178,624 | A |   | 1/1993 | Kyun |
| 5,376,003 | A |   | 12/1994 | Rizkalla |
| 5,379,521 | A | * | 1/1995 | Lynders ................. B26B 29/04 30/233 |
| 5,542,435 | A |   | 8/1996 | Kelly et al. |
| 5,584,840 | A |   | 12/1996 | Ramsey et al. |
| 5,591,173 | A |   | 1/1997 | Schifano |

(Continued)

*Primary Examiner* — Ghassem Alie
(74) *Attorney, Agent, or Firm* — Wood Herron & Evans LLP

(57) ABSTRACT

A releasably attached surgical scissor spray shield is mounted immediately proximate to the scissor blade. The shield controls the spray at the source thus shielding not only the user, but all personnel in the vicinity when an umbilical cord or the like is cut. The mounting mechanisms for the shield releasably, yet securely attaches the spray shield to the scissors so the shield remains immediately proximate to the scissor blades and umbilical cord yet does not restrict the opening of the scissor shear blades. The shield is mounted in close proximity to the cutting operation of the scissors to thereby deflect blood spray immediately adjacent to the source of the spray. The shield does not restrict the operational movement of the scissor blades and arms during the cutting operation.

17 Claims, 14 Drawing Sheets

(56) References Cited

U.S. PATENT DOCUMENTS

| | | | |
|---|---|---|---|
| 5,667,516 A | 9/1997 | Allen | |
| 5,676,672 A | 10/1997 | Watson et al. | |
| 5,787,893 A | 8/1998 | Hoftman | |
| D399,971 S * | 10/1998 | Scherer | D24/130 |
| 5,913,862 A | 6/1999 | Ramsey et al. | |
| 5,925,052 A | 7/1999 | Simmons | |
| 6,129,622 A | 10/2000 | Seaman et al. | |
| 6,132,447 A | 10/2000 | Dorsey | |
| 6,151,783 A * | 11/2000 | Morales | B26B 29/04 30/124 |
| 6,443,958 B1 | 9/2002 | Watson, Jr. et al. | |
| 6,740,095 B2 | 5/2004 | Watson, Jr. et al. | |
| 6,780,195 B2 | 8/2004 | Porat | |
| 7,402,164 B2 | 7/2008 | Watson, Jr. et al. | |
| 8,216,249 B2 | 7/2012 | Watson et al. | |
| 2004/0194319 A1* | 10/2004 | Cook | B26B 29/04 30/233 |
| 2008/0125663 A1* | 5/2008 | Golijanin | A61B 5/0059 600/479 |
| 2010/0064528 A1* | 3/2010 | Habib | B26B 13/16 30/232 |

* cited by examiner

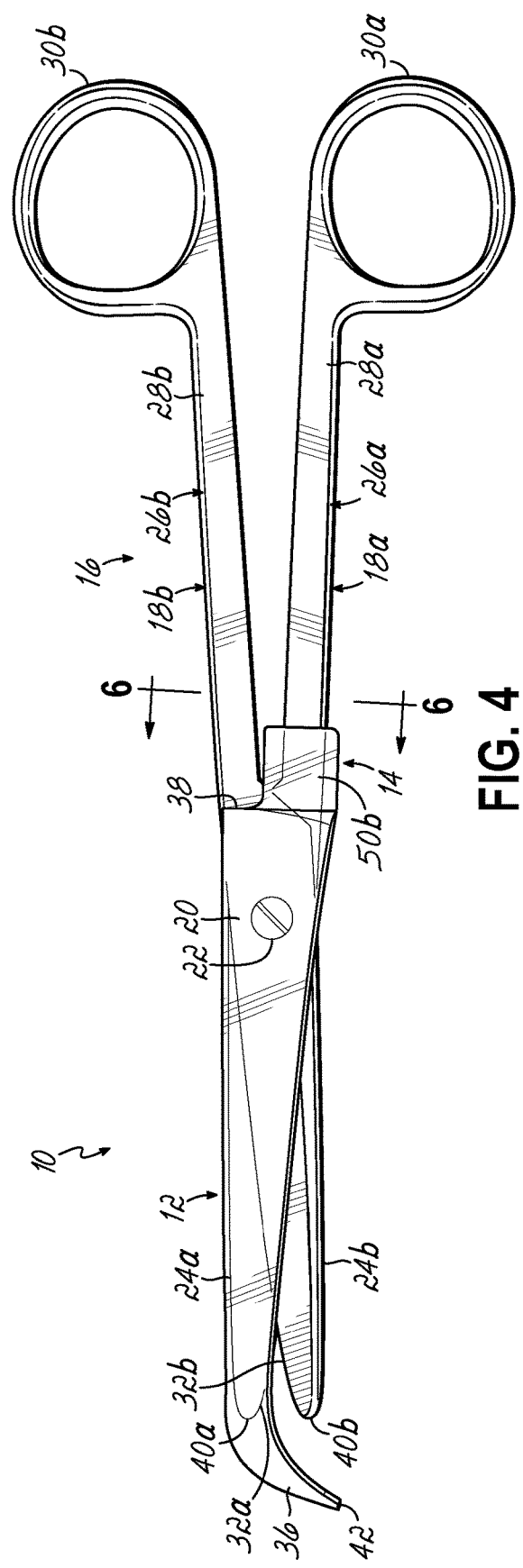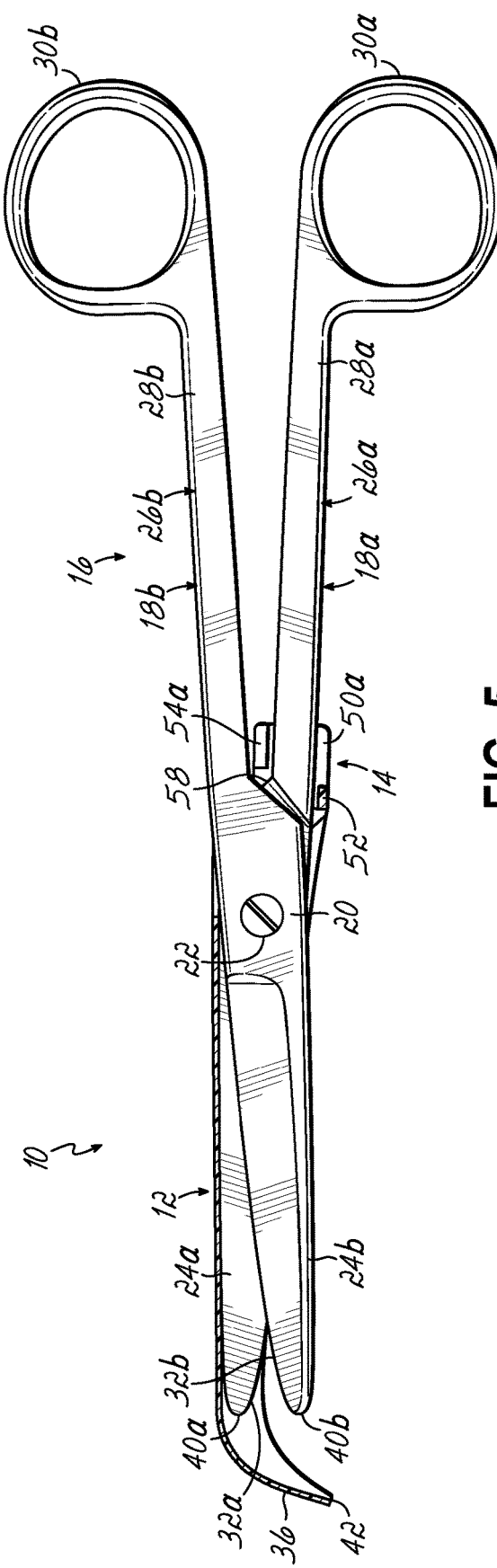

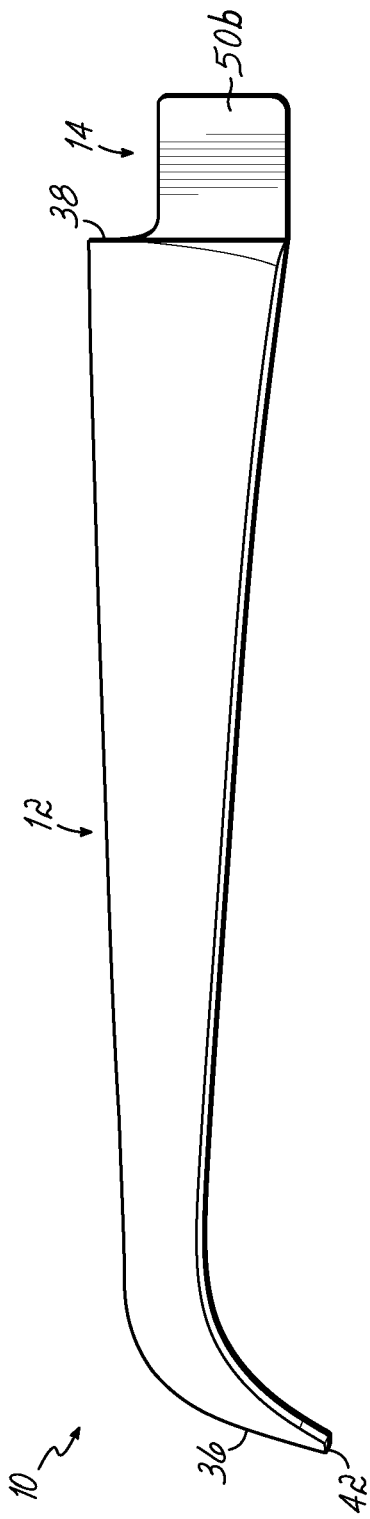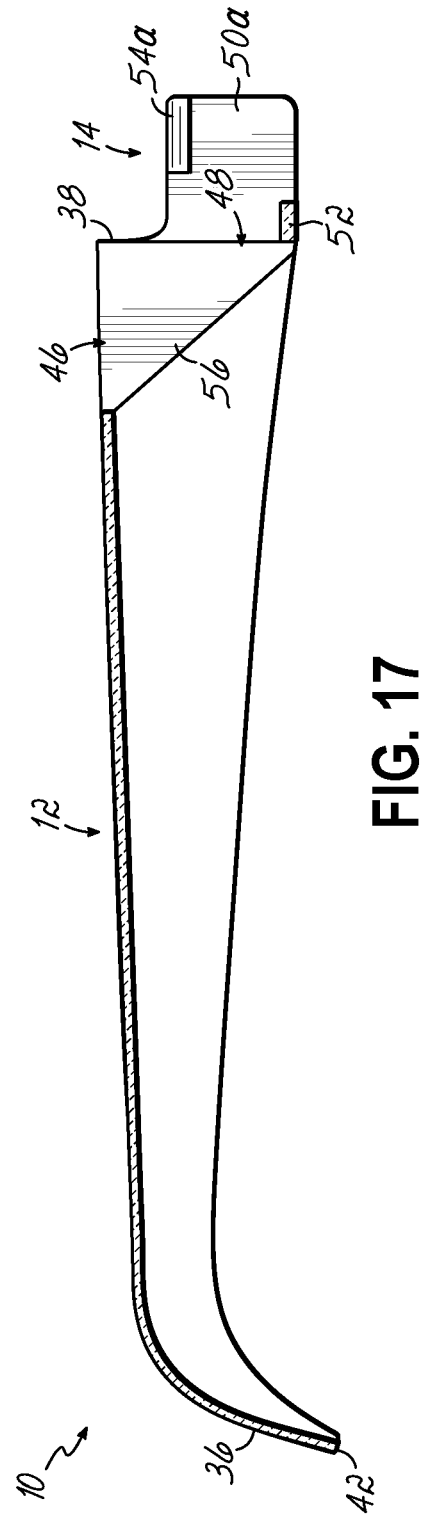

SCISSOR MOUNTED BLOOD SPRAY SHIELD

CROSS REFERENCE TO RELATED APPLICATION

This claims the benefit of U.S. Provisional Patent Application Ser. No. 62/069,886, filed on Oct. 29, 2014, and herein incorporated by reference in its entirety.

BACKGROUND OF THE INVENTION

This invention relates to spray shields primarily for use with surgical scissors to protect people from potentially hazardous blood spray when an umbilical cord or any other item is severed.

For more than fifty years, labor and delivery clinicians have used the same method for transecting the umbilical cord. The process includes placing two clamps on the umbilical cord several inches apart from each other and cutting the umbilical cord between the two clamps with surgical scissors. The blood in the umbilical cord between the two clamps remains pressurized and has been known to spray as far as eight feet or more hitting walls, ceiling tiles, drapes, clinicians and others. It is well established that there exists more than twenty blood borne pathogens such as AIDS/HIV, Hepatitis C, sexually transmitted diseases and now the Ebola virus that could be present in the blood spray and which could contaminate those present. Cases of clinician exposure to blood borne pathogens such as HIV/AIDS and sexually transmitted diseases through cord blood spray are well documented. Such cases require extensive, costly and physically demanding prophylactic treatment.

In spite of numerous technological attempts to address this problem, no commercially or functionally viable devices or solutions are available to clinicians to prevent blood spray when cutting the cord. In the majority of cases, the prior art/devices simply did not function as intended. In one instance, the device attempted to combine functions such as preventing spray while also drawing cord blood into vials. In another example, the device was intended to prevent blood spray while simultaneously cutting and clamping the umbilical cord. Those and other known devices were plagued with operational issues involving one or more of these functions and consequently unable to perform the intended functions to the satisfaction of the market. Devices that required a significant departure from existing procedures and new equipment also met with resistance. As with virtually every decision, cost is an important factor and the cost of some devices were considered prohibitive.

With no functional solution available, clinicians try to minimize the impact of umbilical cord blood spray in several different ways. Many clinicians put a hand up near the scissors to act as a shield. Unfortunately, this prevents the clinician from using that hand for clinical or care related functions and momentarily distracts the clinician causing them to focus on their own safety rather than the immediate procedure and the patient's care and safety.

Another approach is to look away when the cord is cut hoping any spray that might occur will hit them somewhere other than the eyes, nose or mouth. Clearly this is undesirable as it is best to have clinicians looking at the task at hand.

Alternatively, some caregivers have even held a towel over the area in an attempt to block the spray. None of these approaches are effective or safe for either the clinician or the patient. Furthermore, they do not comply with the federal requirements as set forth in 29 CFR 1910 generally requiring that employers reduce the risk of blood borne pathogen exposure to employees.

One attempt to address this problem is disclosed as a disposable shield in U.S. Pat. No. 5,542,435 to Kelly, et al. This device was intended to protect only the scissor user. It does not protect any other personnel in the area due to its shape, orientation, location and distance from the source of the spray.

While protecting the clinician cutting the cord, typically a doctor or midwife, is a worthwhile endeavor, a 2012 survey of labor and delivery nurses (i.e. clinicians not cutting the umbilical cord and positioned in physical locations throughout the delivery area) revealed that 95% of those nurses had experienced cord blood spray and 21% had been sprayed within the prior year. Additionally, tests designed to replicate spray from an umbilical cord were recently conducted and the spray pattern analysis indicated that as much as 50% of the spray occurs in a direction other than towards the user. Blood spray is a serious problem to all in the delivery room and is not limited to the clinician cutting the umbilical cord.

A similar potential solution is disclosed in U.S. Pat. No. D399,971 to Scherer which approaches the problem in a similar manner as does Kelly, et al., but with a different shield design. Nevertheless, Scherer fails to solve the above-noted shortcomings of Kelly, et al.

As previously mentioned, there is currently no functionally or commercially viable solution in the marketplace for the problem of blood spray resulting from the transection of the umbilical cord or other cutting procedures.

SUMMARY OF THE INVENTION

These and other shortcomings in the prior art have been addressed with this invention. In accordance with at least one embodiment of this invention, a releasably attached, surgical scissor disposable spray shield is mounted immediately proximate to the scissors and umbilical cord and addresses these and other shortcomings in the prior art. The shield is immediately proximate to the scissors and umbilical cord and controls the spray at the source thus shielding not only the user, but all personnel in the vicinity when the umbilical cord is cut. The mounting mechanisms for the shield releasably, yet securely attach the spray shield to the surgical scissors so the shield remains immediately proximate to the scissor shear blades and umbilical cord yet does not unnecessarily/functionally restrict the opening of the scissor shear blades. Some of those mounting mechanisms are contemplated herein.

In various embodiments, the scissor mounted blood spray shield according to this invention shields not only the operator of the scissors, but other personnel in the vicinity. In various embodiments, this shield is mounted in close proximity to the cutting operation of the scissors to thereby deflect blood spray immediately adjacent to the source of the spray. Additionally, various embodiments of this invention when mounted to the scissors do not restrict the operational movement of the scissor blades and arms during the cutting operation. Moreover, the shield is securely mounted to the scissors while still avoiding interference with the cutting operation.

Additionally, various embodiments of this invention allow for the shield and scissor combination to stand upright with the scissors in a generally horizontal orientation to allow for easy location by the clinician as well as convenient and easy grasping and manipulation of the scissors and the shield unit.

As such, the above noted and other shortcomings with known devices have been overcome with the scissor mounted blood spray shield according to various embodiments of this invention.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 4 is a side elevational view of the combination of FIG. 1;

FIG. 5 is a view similar to FIG. 6 with the blood spray shield shown in cross-section;

FIG. 16 is a right side elevational view of the blood spray shield of FIG. 12 with the left side elevational view being a mirror image thereof;

FIG. 17 is a cross-sectional view taken along line 17-17 of FIG. 14;

DETAILED DESCRIPTION OF THE INVENTION

Figure 1:
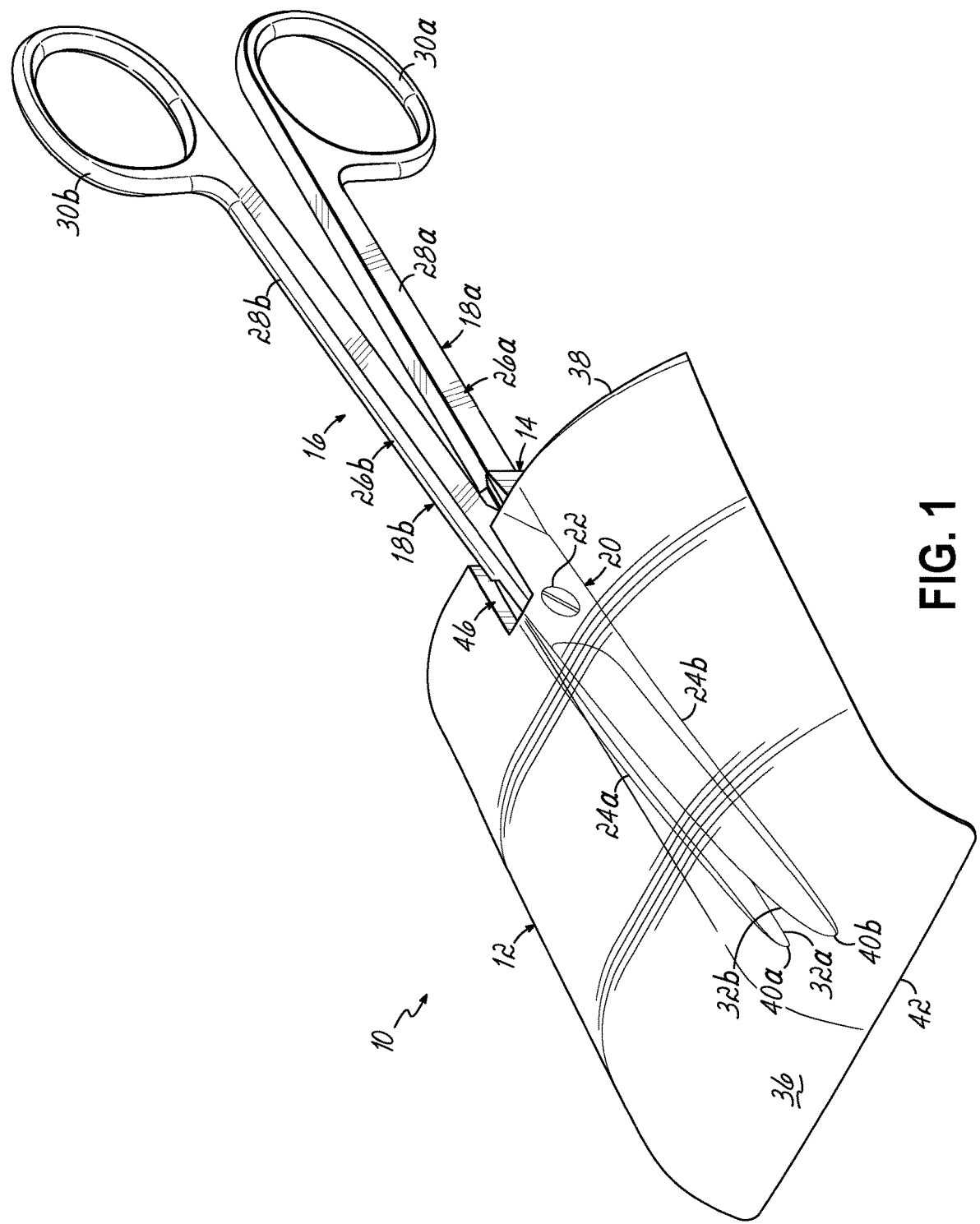
FIG. 1 is a perspective view of one embodiment of a blood spray shield mounted upon a pair of scissors according to this invention.

One embodiment of the surgical scissor disposable spray shield 10 is illustrated in FIGS. 1-19. The surgical scissor disposable spray shield 10 may include a shield portion 12 and a mount 14.

The surgical scissor disposable spray shield 10 according to various embodiments of this invention is intended to be removably mounted to a pair of surgical scissors 16 or another implement. The surgical scissors 16 includes a pair of scissor arms 18a, 18b which are pivotally joined together at a joint 20. The joint 20 includes a pivot member 22 which, in various embodiments, may include a screw, pin or other structural member about which the two scissor arms 18a, 18b pivot or articulate relative to one another generally in a plane that is perpendicular to the pivot axis of the joint 20. Each scissor arm 18a, 18b includes a blade portion 24a, 24b extending from a distal end of the joint 20, a tip 40a, 40b and an arm portion 26a, 26b extending proximally from the joint 20. The arm portions 26a, 26b may include an elongate handle 28a, 28b with a grip 30a, 30b in the form of a loop or eyelet at the terminal end of the arm portion 26a, 26b. Each blade portion 24a, 24b may include a sharpened scissor blade 32a, 32b which cooperates with the sharpened scissor blade 32b, 32a of the complimentary scissor arm 18a, 18b to cut, sever, transect or otherwise slice through a typical scissor cutting action any member such as an umbilical cord 34 or the like which may be positioned between the articulating blade portions 24a, 24b of the surgical scissors 16. The scissor arms 18a, 18b pivot about a pivot axis defined by the joint 20 to and between open positions and a closed position in which the blade portions 24 are closed upon each other. While one specific embodiment of a pair of scissors is shown and described herein, it will be readily appreciated by one of ordinary skill in the art that this is but an exemplary tool on which the spray shield according to various embodiments of this invention may be temporarily mounted within the scope of this invention.

Figure 2:
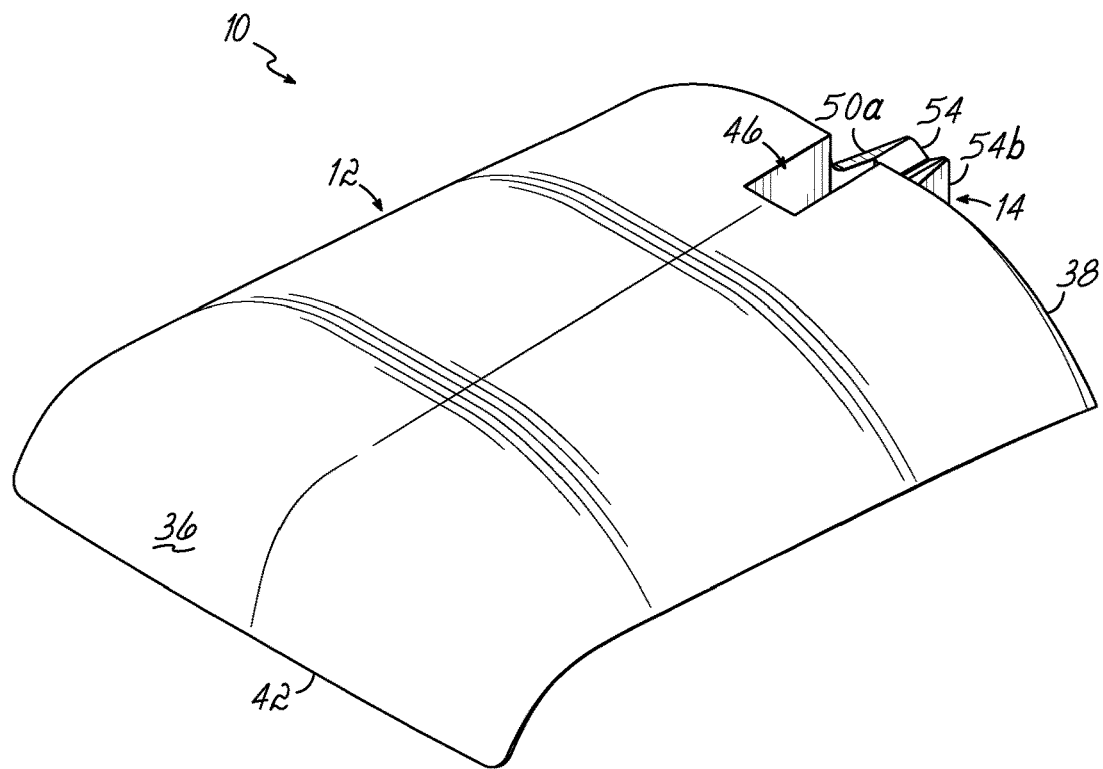
FIG. 2 is a top perspective view of the blood spray shield of FIG. 1.
Figure 3:
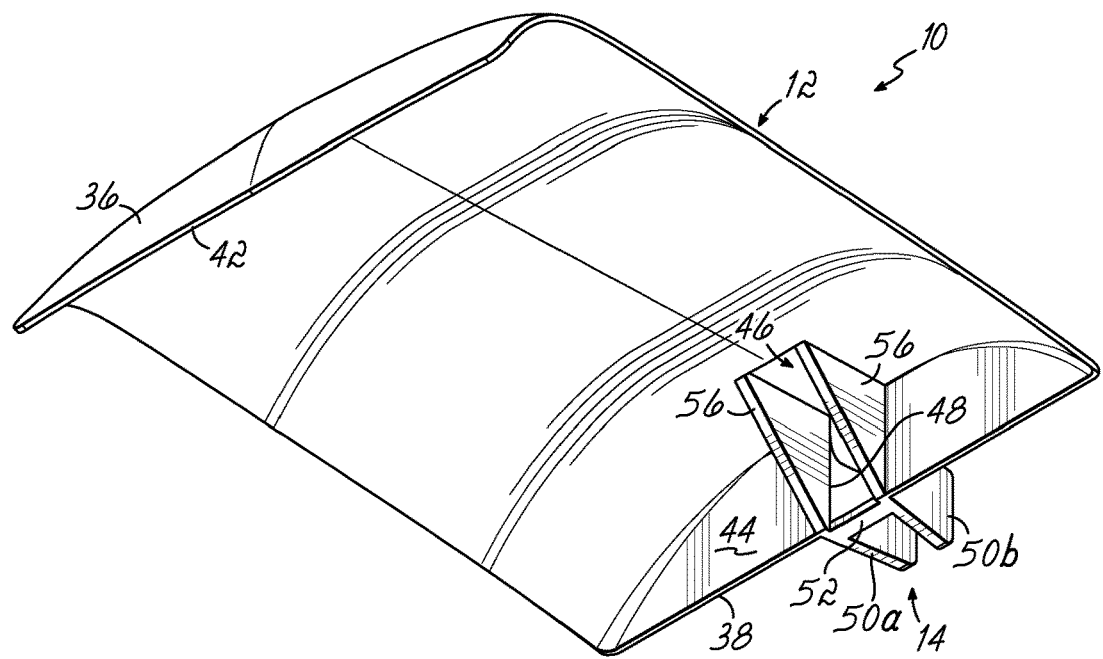
FIG. 3 is a bottom perspective view of the blood spray shield of FIG. 1.

The shield portion 12 could be of many different shapes, but in one embodiment may be concave and take the approximate form of a volumetric cross-section of a shape that resembles a cylinder with an ellipsoidal or torispherical dome end cap 36 as shown in FIGS. 1-3. The shield portion 12 may have a thickness of approximately 0.70 mm and may be approximately 80 mm in length at the longest point and approximately 65 mm wide at its widest point. The horizontal dimensions or height along the length of the shield portion 12 cylindrical section's volumetric cross section may follow the horizontal dimensions or height of the upper blade portion 24a to which it is immediately proximate and range from approximately 13 mm at the rear end 38 of the cylindrical portion to approximately 5 mm at the ellipsoidal end cap 36 of the cylindrical portion of the shield portion 12 (See FIG. 1). The ellipsoidal end cap 36 at the very front end of the shield portion 12 may extend vertically down in front of an upper blade tip 40a of the scissor lower arm 18a approximately 13 mm (See FIG. 5). The ellipsoidal end cap 36 at the very front end of the shield portion 12 which may extend vertically down in front of the upper blade tip 40a of the scissor lower arm 18a may have a flat edge 42 extending horizontally across the very bottom of the ellipsoidal end cap 36 (See FIG. 1).

A rear shield 44 extends down perpendicularly approximately 13 mm at the rear end of the shield portion 12 (See FIG. 3). At the rear end of the shield portion 12, there is a void or shield portion cutout 46 in the middle of the shield portion 12. The shield portion cutout 46 begins at the very end of the shield portion 12 where the shield portion 12 intersects the rear shield 44 and continues lengthwise toward the front of the shield portion 12 and ends at a forward edge (See FIG. 2). The shield portion cutout 46 is approximately 7 mm wide and 11 mm long in one embodiment. The dimensions of the shield portion cutout 46 may be dependent on the size of the surgical scissors 16 which are compatible with the surgical scissor disposable spray shield 10. The width of the shield portion cutout 46 may be determined by the width of the surgical scissors 16 at the joint 20 and the length may be determined by the width of the upper blade portion 24a at that point and may vary depending on the size of the surgical scissors 16. The apex of the shield portion 12 is located at the midpoint of the width of the shield portion 12 and runs lengthwise down the shield portion 12 and may have a 2° angle of declination from a line parallel to the upper arm portion 26b. This 2° angle of declination approximates the angle of declination between a line parallel to the surface of the upper or non-shearing edge of the upper blade portion 24a and a line parallel to the upper arm portion 26b.

FIG. 3 shows one view of the rear shield 44. The rear shield 44 may generally take the shape of a lengthwise bisected ellipse and may be approximately 65 mm wide at the widest point and approximately 13 mm tall at the tallest point. The rear shield 44 may contain a rear shield vertical opening 48. The rear shield vertical opening 48 may be located at the midpoint of the major dimension of the rear shield 44 and may extend the entire height of the rear shield 44. The rear shield vertical opening 48 is approximately 7 mm wide in one embodiment.

Figure 12:
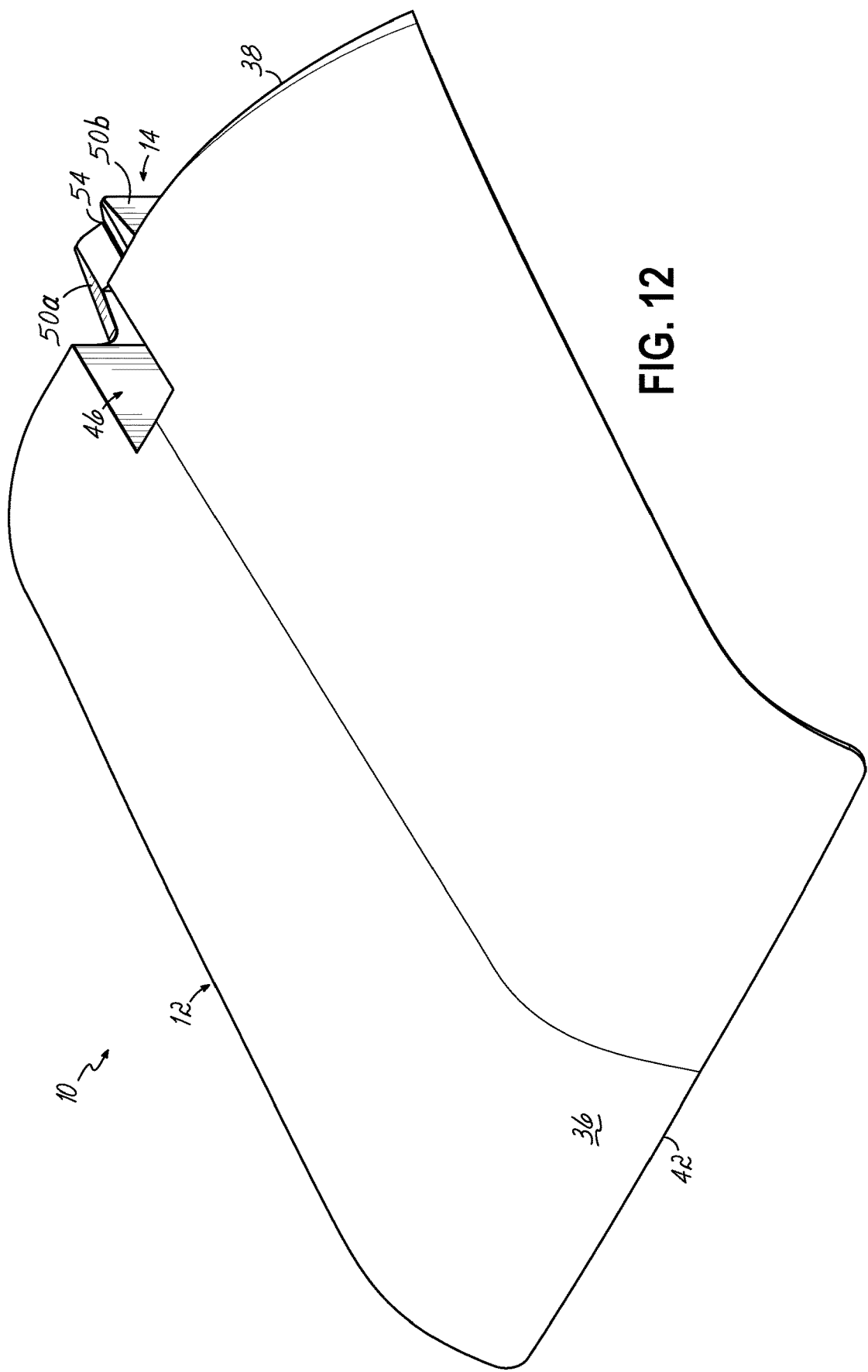
FIG. 12 is a top perspective view of a blood spray shield according to one embodiment of this invention.
Figure 13:
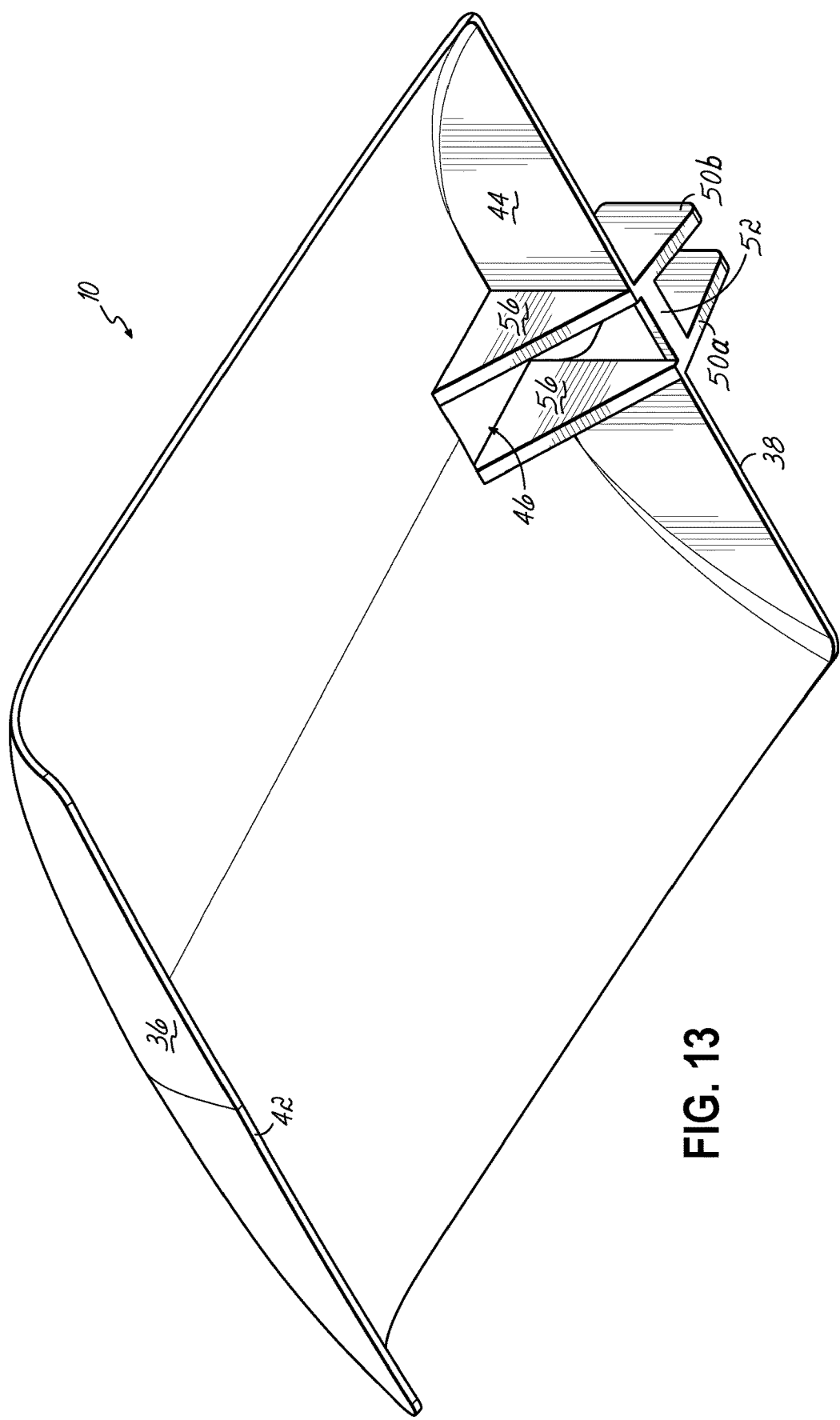
FIG. 13 is a bottom perspective view of the blood spray shield of FIG. 12.
Figure 14:
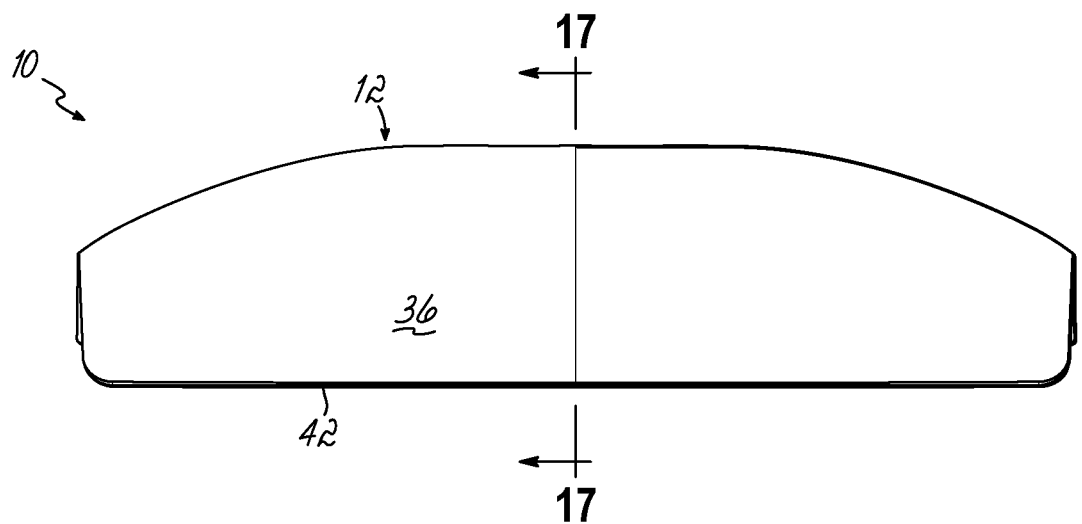
FIG. 14 is a front elevational view of the blood spray shield of FIG. 12.
Figure 15:
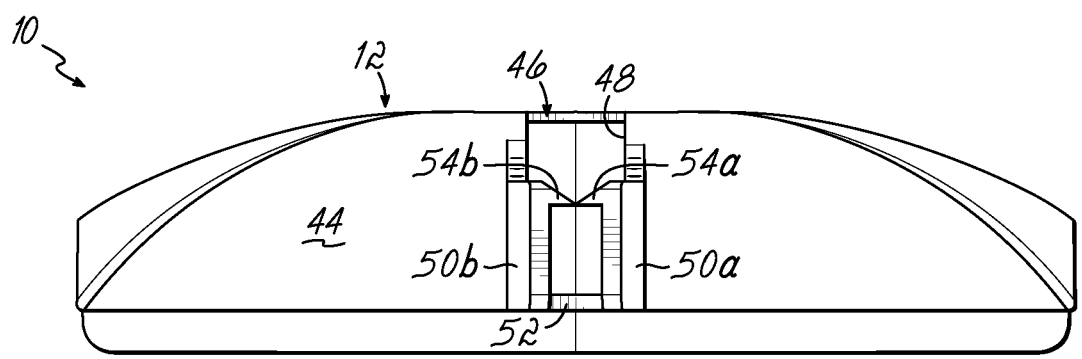
FIG. 15 is a rear elevational view of the blood spray shield of FIG. 12.
Figure 18:
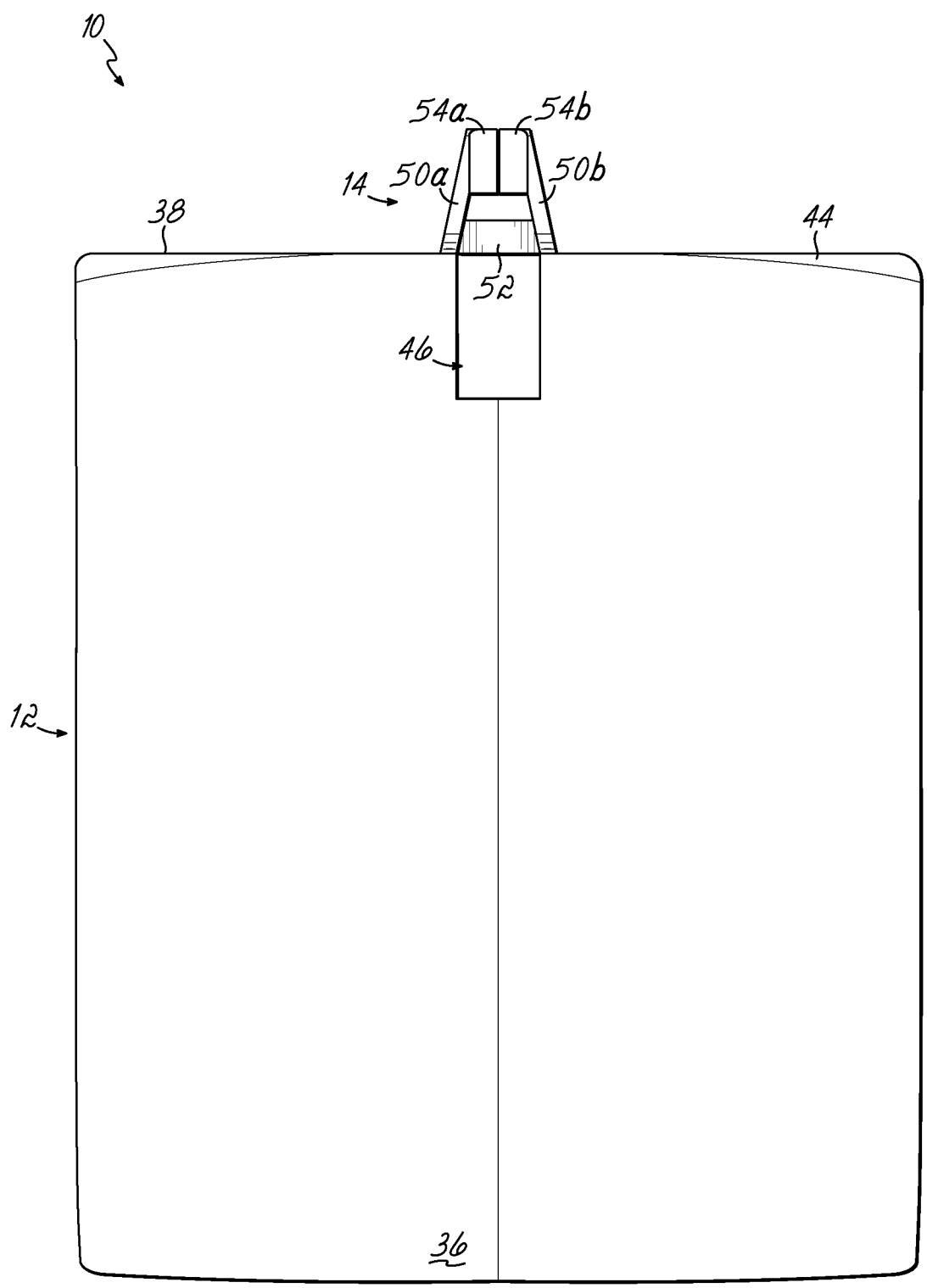
FIG. 18 is a top view of the blood spray shield.
Figure 19:
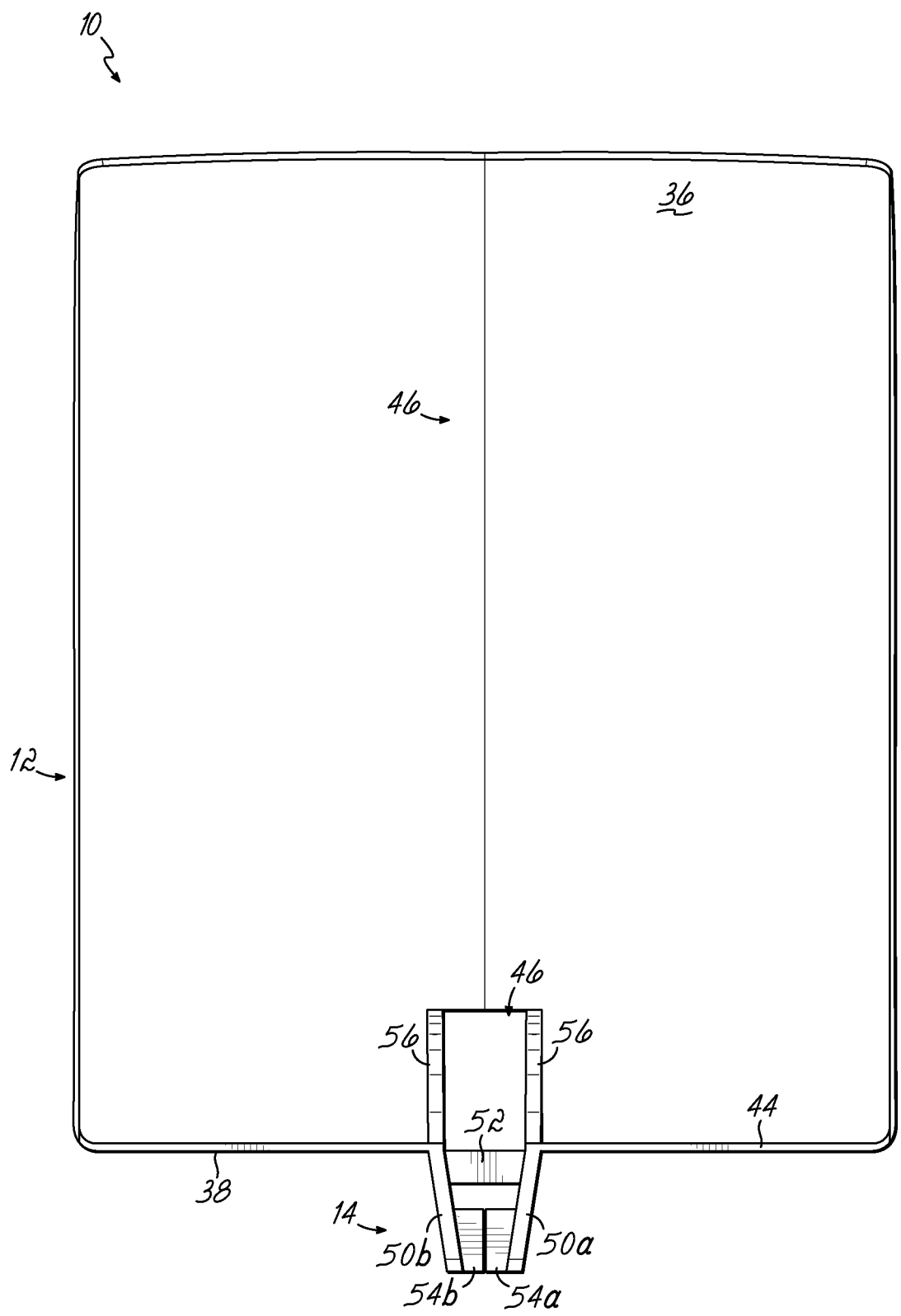
FIG. 19 is a bottom view thereof.

FIG. 12 shows a top view and FIG. 13 shows a bottom view of the mount 14 of one embodiment of this invention. The mount 14 may include two opposable arms 50a, 50b, a lower detent 52 and an upper detent 54. The lower and upper detents 52, 54 may be referred to as first and second detents or second and first detents. The mount 14 of this embodiment is approximately 28 mm in length. The opposable arms 50a, 50b may be directly connected to their respective sides of the rear shield vertical opening 48 of rear shield 44 and be approximately 7 mm apart from each other at the rear shield vertical opening 48. A portion of the mount 14 may be located underneath the shield portion 12 and inside the rear shield 44. The top surfaces of the portion of the mount 14 located underneath the shield portion 12 may also be connected to the underside of the shield portion 12. The mount portions 56 of the mount 14 located underneath the shield portion 12 and inside the rear shield 44 could be several different shapes, but in this embodiment are triangular.

In one embodiment, the lower detent 52 may be approximately 7 mm wide, 2 mm long and approximately 1 mm high and may be located at the bottom of and approximately equidistant lengthwise along the mount 14. In alternative embodiments, the lower detent 52 could be comprised of one continuous member connected at both opposable arms as in this embodiment, or two individual members very similar to the upper detent 54, each connected to an opposable arm 50a, 50b and meeting each other in the middle between the opposable arms 50a, 50b, or one member having a triangular shape similar to a member of the upper detent 54, connected only to the right opposable arm 50b and extending between 50% and 99% of the distance between opposable arms 50a, 50b. The lower detent 52 may serve three purposes. The first purpose is to serve as a stop for the lower blade portion 24b and provide horizontal stability for the surgical scissor disposable spray shield 10 on the surgical scissors 16. The lower detent 52 coupled with the forward edge of the shield portion cutout 46 may prevent the upper arm portion 26b from rotating more than 90° and pushing the surgical scissor disposable spray shield 10 too far forward on the surgical scissors 16. The second purpose of the lower detent 52 may be to prevent the scissor arm portions 26a, 26b from moving vertically down past that point and coupled with the upper detent 54 may help provide vertical stability for the surgical scissor disposable spray shield 10 on the surgical scissors 16. The third purpose may be to provide stability and act as an anchor point for the opposable arms 50a, 50b to ensure the opposable arms maintain sufficient compressive force on the lower arm portion 26a and do not flex too much. However, the surgical scissor disposable spray shield 10 with the mount 14 integrally molded to the rear shield 44 and shield portion 12, may be sufficiently secure to hold the mount 14 in place at those connected locations keeping the moment arm sufficiently close to the rear of the mount 14 and preventing the opposable arms 50a, 50b from excess movement. In that case, the lower detent 52 could be designed similar to the upper detent 54 with triangular shape pointing down rather than up. This has the advantage of providing an additional or optional scissor mounting mechanism whereby the surgical scissor disposable spray shield 10 could be forced down onto the surgical scissors 16 from the top rather than the surgical scissors 16 being forced down on the surgical scissor disposable spray shield 10 from the top. A lower detent that allows the opposable arms 50a, 50b to be more independent of each other may strengthen the opposable arms 50a, 50b. The lower and upper detents 52, 54 also provide a more secure connection of the surgical scissor disposable spray shield 10 to the surgical scissors 16 so that during operation of the surgical scissors 16 the shield portion 12 remains in a fixed or generally constant position relative to one or both of the scissor blades 24.

The horizontal distance from the forward or front edge of the lower detent 52 and the forward edge of the shield portion cutout 46 is approximately 11 mm, but this may be dependent on the size of the surgical scissors 16. This horizontal distance may be determined by the width of the lower blade portion 24b at that point and may vary depending on the size of the surgical scissors 16.

Figure 7:
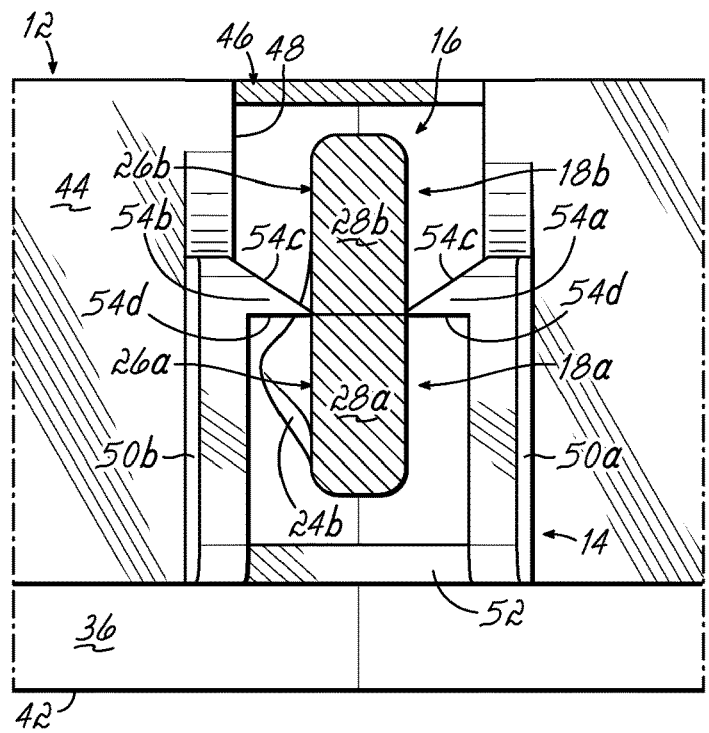
FIG. 7 is a view similar to FIG. 6 with the scissors in a closed configuration.
Figure 8:
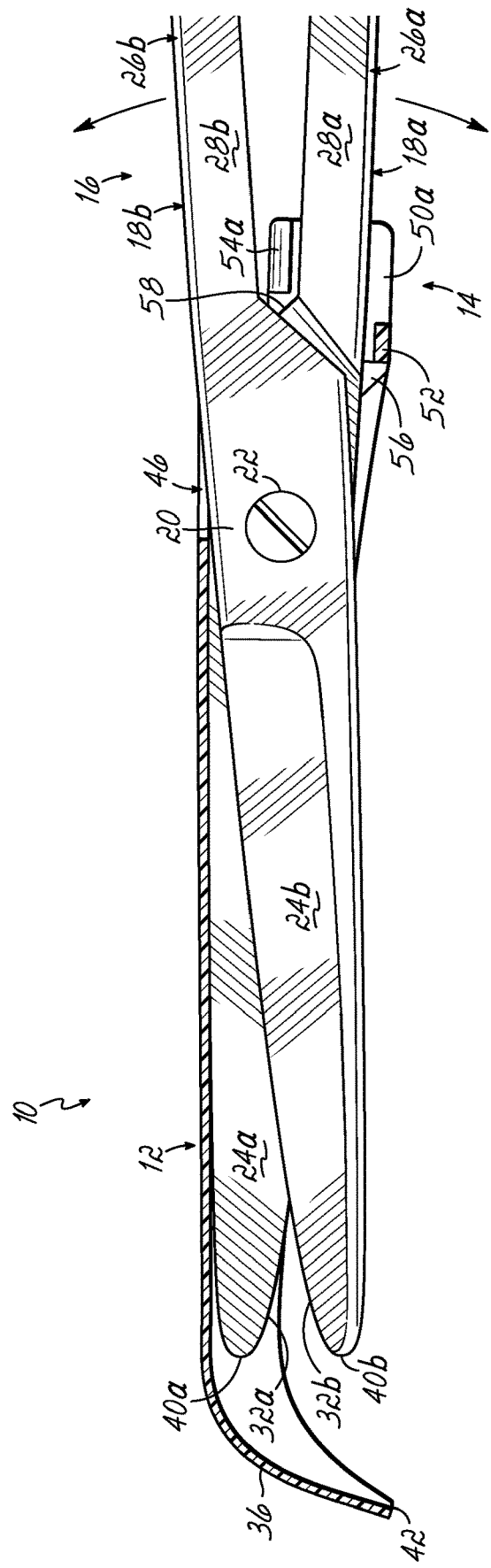
FIG. 8 is a side elevational view with the blood spray shield in cross-section and the scissors in an opening operation.
Figure 9:
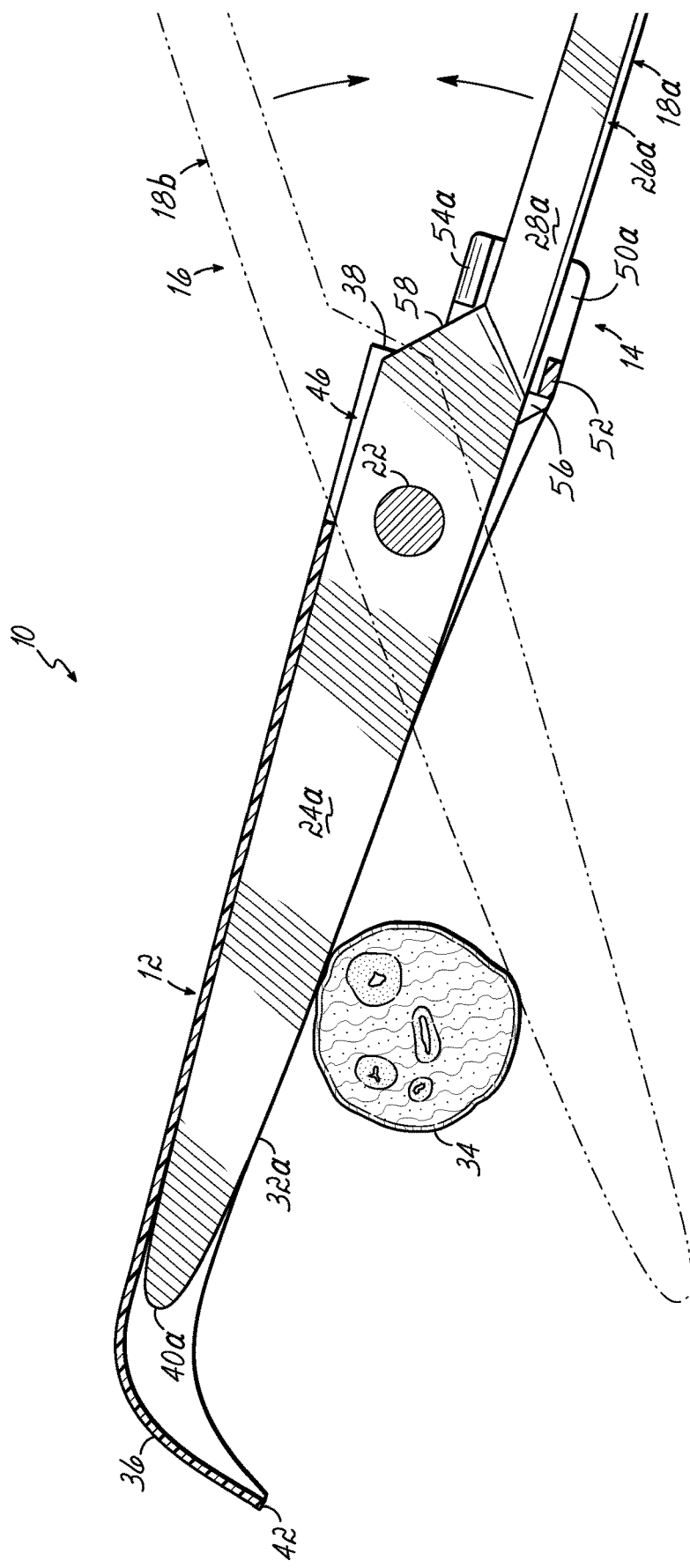
FIG. 9 is a view similar to FIG. 8 with an umbilical cord positioned between the blades of the scissors in a closing operation.
Figure 10:
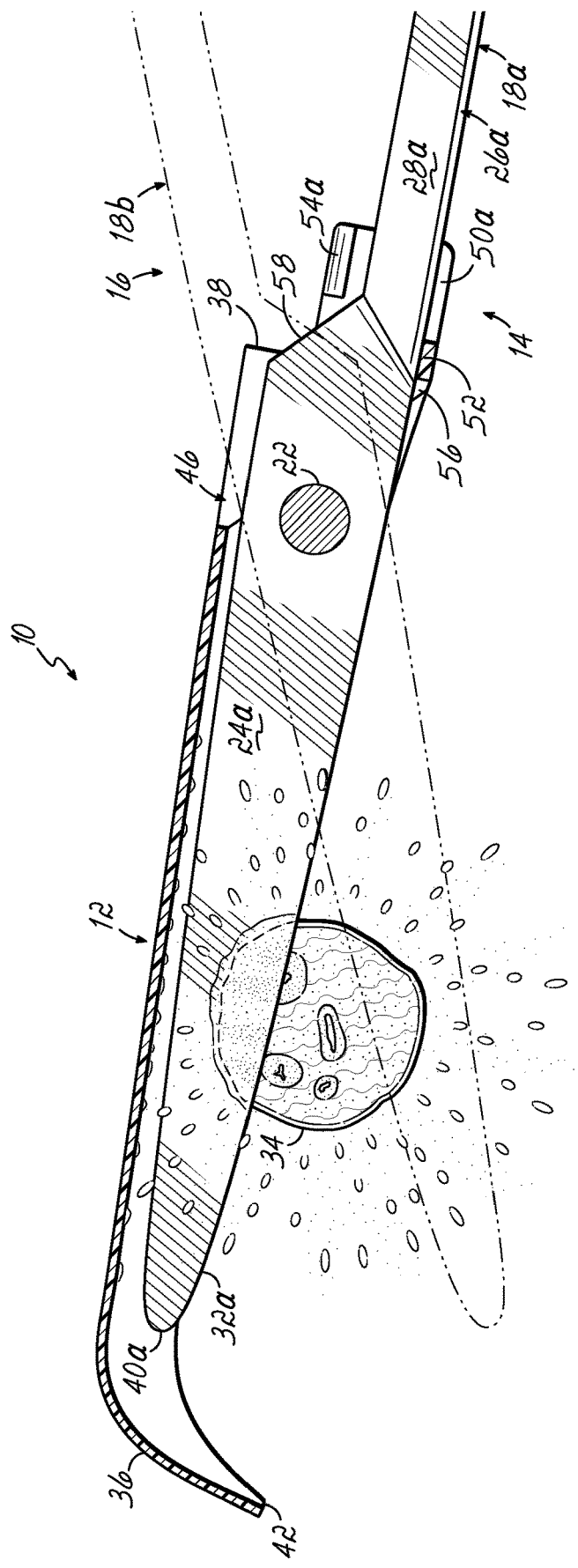
FIG. 10 is a view similar to FIG. 9 with the umbilical cord being cut and the blood spray shield containing spray from the cutting action of the scissors.

FIG. 7 illustrates how the upper detent 54 may be located at the top rear end of the mount 14 and comprised of two opposing members; upper detent opposing member 54a and upper detent opposing member 54b located opposite each other on each of the opposable arms 50a, 50b, respectively. Upper detent opposing member 54a and the upper detent opposing member 54b are individually approximately 2 mm wide, 5 mm long and may be of a generally triangular shape ranging from approximately 0.2 mm at its narrowest point to approximately 2 mm at its highest point.

Figure 6:
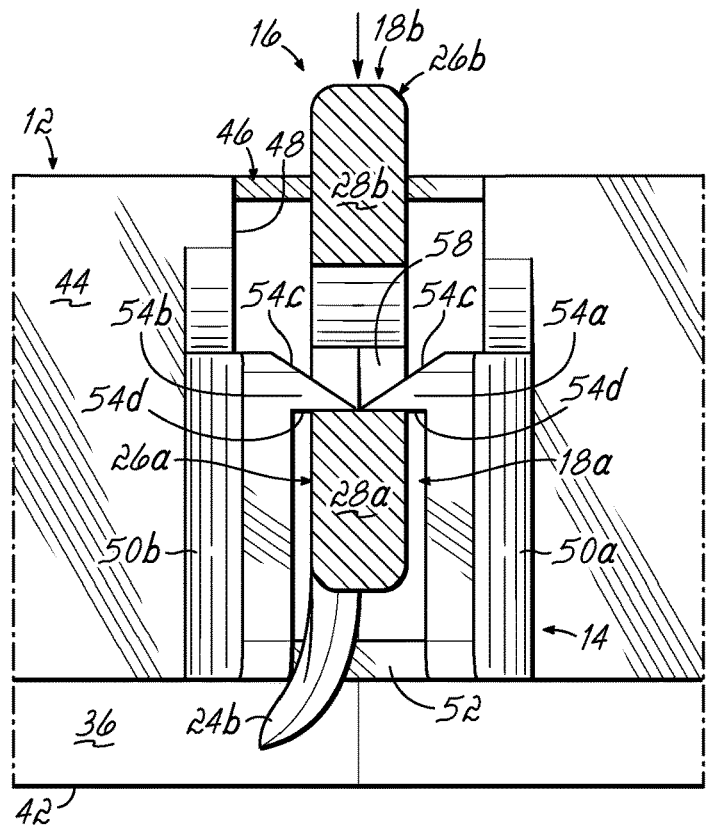
FIG. 6 is a cross-sectional view taken along line 6-6 of FIG. 4.

The upper detent opposing members 54a, 54b may be of a generally triangular shape forming an incline plane with the upper detent opposing member incline plane side 54c facing up and away from the mount 14 as illustrated in FIG. 7. The upper detent opposing member short side of each of the respective upper detent opposing members 54a, 54b may be attached to, comprise or be part of their respective opposable arms 50a, 50b per FIG. 7. The upper detent opposing member base side 54d of each of the respective upper detent opposing members 54a, 54b of the upper detent 54 faces downward as shown in FIG. 6.

The vertical distance between the top side of the lower detent 52 and the bottom side of the upper detent 54 or the upper detent opposing member base side 54d is approximately 6 mm. This dimension may be the height of the lower arm portion 26a and may vary depending on the size of the surgical scissors 16. The horizontal distance from the leading or front edge of the lower detent 52 and the leading or front edge of the upper detent 54 may be approximately 12 mm. This dimension may be dependent on the size of the surgical scissors 16. This horizontal distance is determined by the distance from the rear or non-cutting edge of the lower blade portion 24b when it is perpendicular to the upper blade portion 24a and the rear edge of the scissor joint 20 area at the scissor joint area projection 58 (FIG. 8) and may vary depending on the size of the surgical scissors 16. The horizontal distance between the forward edge of the upper detent 54 and the forward edge of the shield portion cutout 46 may be approximately 23 mm and may vary depending on the size of the surgical scissors 16.

In various embodiments of this invention, the lower and upper detents 52, 54 may be closely spaced or in contact with the adjacent portions of the first scissor arm portion 26a as shown in FIG. 5. This snug or tight fitting relationship for the mount 14 on the surgical scissors 16 allows for the shield portion 12 to move with the upper blade portion 24a during the cutting operation of the surgical scissors 16 and remain a fixed distance from the upper blade portion 24a.

The opposable arms 50a, 50b may be canted in towards each other beginning at the lower detent 52 as illustrated in FIG. 13. The cant angle for opposable arm 50a, 50b may be approximately 9°. At the rear end of the mount 14, the opposable arms 50a, 50b may be approximately 3.5 mm apart from each other.

The surgical scissor disposable spray shield 10 may be made from any material including clear polymeric material. In one embodiment it is made of polycarbonate.

To attach the surgical scissor disposable spray shield 10 to the surgical scissors 16, the user grasps the surgical scissor disposable spray shield 10 with one hand and with the mount 14 towards the user. The user inserts the closed scissor blade tips 40a, 40b into the rear shield vertical opening 48 (FIG. 3) above the lower detent 52 (FIG. 3) and below the forward edge of the shield portion cutout 46 (FIG. 2). At this time, the lower arm portion 26a and upper arm portion 26b will both be above the upper detent 54. The user continues to insert the scissor blade tips 40a, 40b until the scissor joint 20 is past the rear shield 44.

At this point, while firmly holding the surgical scissor disposable spray shield 10 with one hand, the user then moves the lower arm grip 30a down which will force the lower arm portion 26a down onto the upper detent 54 and down the incline plane created by the generally triangular shape of the upper detent opposing members 54a, 54b (See FIGS. 6-7). The lower arm portion 26a may be wider than the rear end of the mount 14 so as the lower arm portion 26a is continually forced down onto the upper detent 54 the upper detent opposing members 54a, 54b and the opposable arms 50a, 50b will be forced to move horizontally outward away from the scissor lower arm 18a. The user will continue to force the lower arm portion 26a down onto the upper detent 54 until such time as the lower arm portion 26a is pushed below the upper detent 54 (FIG. 2). The triangular shape design of the upper detent opposing members 54a, 54b and specifically the location of the upper detent opposing member incline plane side 54c (FIG. 6) of the upper detent opposing members 54a, 54b (FIG. 7) is to allow the lower arm portion 26a to slide below the upper detent 54 and to reduce the amount of force required to slide the lower arm portion 26a down and below the upper detent 54. Once the lower arm portion 26a has been pushed below the upper detent 54, the lower arm portion 26a will now push up against and be held firmly in place against the upper detent opposing member base side 54d as illustrated in FIG. 6. The surface of the upper detent opposing member base side 54d is flat and oriented parallel to the top surface of the scissor lower arm 18a (FIG. 6) and is designed to contact and prevent the scissor lower arm 18a from inadvertently slipping or moving up past the upper detent 54 and potentially dislodging or dislocating the surgical scissor disposable spray shield 10 from the surgical scissors 16. The bottom surface of the scissor lower arm 18a may be seated against the lower detent 52.

Once the scissor lower arm 18a is pushed below the upper detent 54, the opposable arms 50a, 50b, having been dislocated or pushed outward from their original position by the scissor lower arm 18a, will seek but be unable to return to their original position. This dislocation and inability of the opposable arms 50a, 50b to return to their original position is an intended result of the cant in the opposable arms 50a, 50b which causes the width of the opposable arms 50a, 50b at the rear end of the mount 14 to be narrower than the width of the scissor lower arm 18a. Additionally, the fact that the opposable arms 50a, 50b move independent of each other in equal yet opposite directions creates equal and opposite forces as a result of their dislocation. The opposable arms 50a, 50b are securely attached to the rear shield 44 at the rear shield vertical opening 48. The opposable arms 50a, 50b may extend the entire height of the rear shield 44 at the attachment location. Furthermore, the top portions of the opposable arms 50a, 50b that are located inside the rear shield 44 and under the shield portion 12 are attached to the underside of the shield portion 12. This design provides security and stability to the opposable arms 50a, 50b and positions the flex point of the opposable arms 50a, 50b sufficiently close to the rear end of the mount 14 such that the force exerted by the opposable arms 50a, 50b on the scissor lower arm 18a when displaced by scissor lower arm 18a will be sufficient to hold the mount 14 securely on the surgical scissors 16 and help prevent the mount 14 from inadvertently moving horizontally or forward or backward along the scissor lower arm 18a during normal scissor operation. Additionally, this allows the shield portion 12 to be fixed relative to the upper blade portion 24a during cutting operations.

The user can then position the mount 14 on the scissor lower arm 18a by sliding the mount 14 forward until the upper detent 54 is pressed up against a scissor joint area projection 58 (see FIG. 5) and the mount 14 can no longer be easily pushed forward. Furthermore, the surgical scissor disposable spray shield 10 has a self-correcting positioning mechanism when the scissor upper arm 18b and scissor lower arm 18a are opened. If the mount 14 is initially positioned too far back on the scissor lower arm 18a, opening of the scissor upper arm 18b and scissor lower arm 18a will cause the scissor upper arm 18b to contact the forward edge of the shield portion cutout 46 and move the mount 14 forward on the scissor lower arm 18a. If the mount 14 is initially positioned too far forward on the scissor lower arm 18a, opening of the scissor upper arm 18b and scissor lower arm 18a will cause the lower blade portion 24b to contact the lower detent 52 and force the mount 14 to slide towards the rear of the scissor lower arm 18a. The mount 14 will be properly positioned when the most forward portion of the upper detent 54 rests against the scissor joint area projection 58 of the scissor lower arm 18a and is no longer capable of moving forward. This proper shield positioning also occurs when the upper blade portion 24a and scissor lower blade portion 24b are perpendicular to each other.

Once the surgical scissor disposable spray shield 10 is properly installed on surgical scissors 16, the lower detent 52 and the upper detent 54 help hold the mount 14 in proper vertical alignment on the scissors (See FIG. 5). The lower detent 52 prevents the mount 14 from moving upward past the lower arm portion 26a while the upper detent 54 helps hold the mount 14 from moving downward past the lower arm portion 26a. The position of the shield portion 12 is fixed relative to the upper blade portion 24a by the mount 14. The upper detent 54 and the lower detent 52 combined with the shield portion 12 resting securely on the upper sharpened scissor blade 32a due to the shield portion 12 angle of declination provide vertical security and stability for the surgical scissor disposable spray shield 10 when mounted on surgical scissors 16. In addition to providing vertical positioning and stability, the upper detent 54 is intended to properly align the mount 14 horizontally on the lower arm portion 26a when the upper detent 54 is positioned all the way forward and against the scissor joint area projection 58. The upper detent 54 also acts as a forward stop for mount 14 preventing the mount 14 from sliding any further forward past the scissor joint area projection 58.

Figure 11:
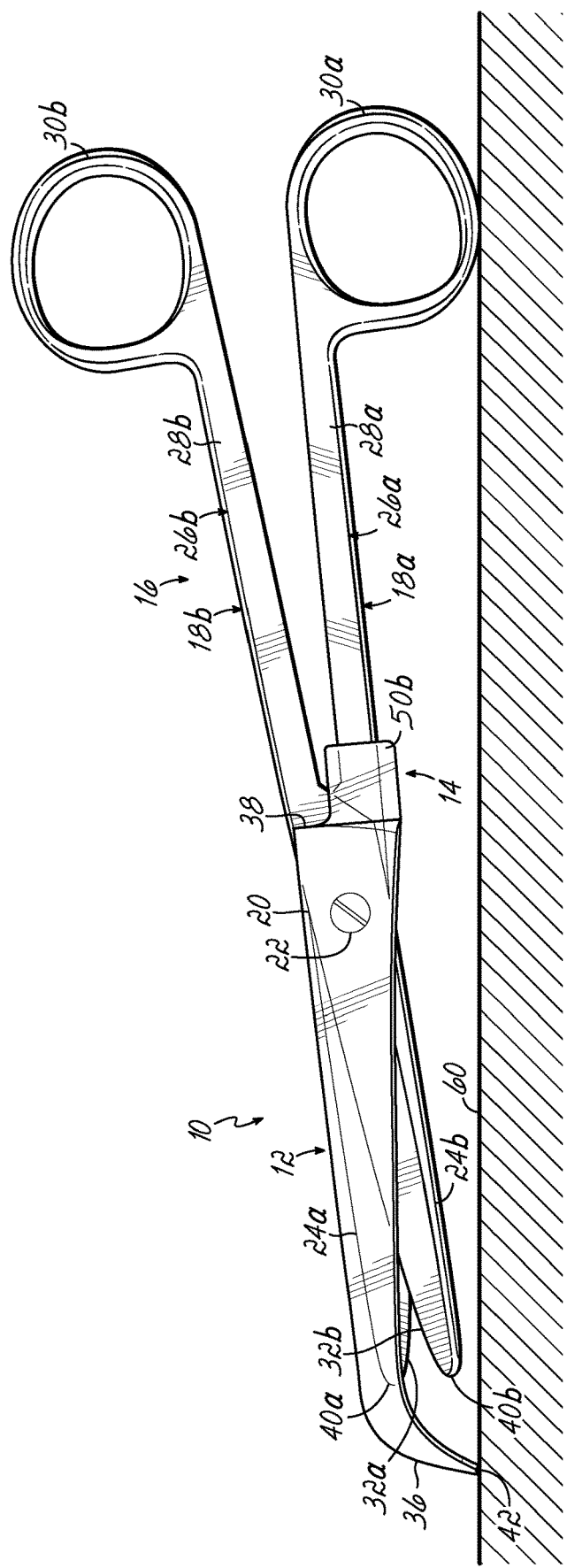
FIG. 11 is a side elevational view of the combination of FIG. 1 positioned upon a supporting surface.

The shield portion 12 rests on and extends over the top, front and sides of the upper sharpened scissor blade 32a. The shield portion 12 may be in closest proximity, above the scissor upper shear blade 32a and around the sides of the umbilical cord 34 and the scissor upper shear blade 32a and scissor lower shear blade 32b during the cutting operation. Once the surgical scissor disposable shield 10 has been properly attached to the surgical scissors 16, the flat edge 42 which extends horizontally across the very bottom of the ellipsoidal end cap 36 at the very front end of the shield portion 12 (See FIG. 11) provides a sufficiently stable base which allows the surgical scissors 16 and surgical scissor disposable spray shield 10 to stand "upright" or generally perpendicular to a supporting surface 60 as shown in FIG. 11 when the surgical scissors 16 are closed or nearly closed. This allows the clinician to more easily and quickly access the surgical scissors 16 with the surgical scissor disposable spray shield 10 attached. In alternative embodiments, the rear spray shield 44 and/or mount 14 may extend sufficiently downward to support the surgical scissors 16 on the supporting surface 60 alone or in combination with the flat edge 42.

When it is time to cut the umbilical cord 34, the clinician easily and quickly picks up the surgical scissors 16 with surgical scissor disposable spray shield 10 attached. The clinician then opens the scissor upper arm 18b and the scissor lower arm 18a which in turn opens the upper sharpened scissor blade 32a and the lower sharpened scissor blade 32b. The scissor upper arm 18b, which is above the upper detent 54, can be rotated a full 90° from the scissor lower arm 18a until the top portion of the scissor upper arm 18b reaches the front edge of the shield portion cutout 46 and the non-cutting edge of the lower sharpened scissor blade 32b reaches the forward edge of the lower detent 52. Throughout the sequence of the upper sharpened scissor blade 32a and lower sharpened scissor blade 32b opening, the shield portion 12 remains in the desired position firmly affixed to the top of and immediately proximate to the upper blade portion 24a. At all times during scissor operations, the shield portion 12, being immediately proximate to the upper blade portion 24a, follows the motion of the upper blade portion 24a.

Once the scissor disposable spray shield 10 is properly positioned on the surgical scissors 16, the umbilical cord 34 or any member can be placed at a location between the sharpened scissor blades 32a, 32b as desired by the user. Once the umbilical cord 34 is in the desired location between the sharpened scissor blades 32a, 32b, the user begins the cutting motion by closing the upper arm grip 30b and the lower arm grip 30a together which in turn causes the sharpened scissor blades 32a, 32b to close against each other.

The upper detent opposing members 54a, 54b may be of a generally triangular shape and dimensions to allow the upper arm portion 26b to fully close against the lower arm portion 26a. This allows the sharpened scissor blades 32a, 32b to fully close or shear against each other. As the upper arm portion 26b is pushed down or closed toward the lower arm portion 26a, the upper arm portion 26b comes in contact with the upper detent opposing member incline plane side 54c and forces the upper detent opposing members 54a, 54b and opposable arms 50a, 50b out perpendicularly from the upper arm portion 26b and lower arm portion 26a. The opposable arms 50a, 50b continue to be forced away from each other until the upper arm portion 26b and lower arm portion 26a are fully closed against each other. Forcing the opposable arms 50a, 50b out from the upper arm portion 26b and lower arm portion 26a places additional compressive force on the lower arm portion 26a by the opposable arms 50a, 50b which serves to even more securely hold the mount 14 in the desired horizontal position on the lower arm portion 26a.

The shield portion 12 continues to remain in the desired position in close proximity to the upper blade portion 24a and is also now above and around the sides of the upper blade portion 24a and lower blade portion 24b as well as the umbilical cord 34. As a result all personnel are protected from blood spray emanating up and out from the umbilical cord 34 preventing potential mucous membrane exposure of the eyes, mouth and nose. In this embodiment, the shield portion deflects any spray discharged from the umbilical cord 34 during or after cutting and provides spray protection for the entire hemisphere above the surgical scissors 16. This spray protection may be even greater depending upon the geometry of the shield portion 12. The ability of the mount 14 to securely position the disposable spray shield 10 on the surgical scissors 16 and in particular the shield portion 12 in close proximity to the upper blade portion 24a and to maintain such position during movement of the upper blade portion 24a provides for advantageous spray protection for the user and others nearby to deflect spray from the umbilical cord 34 being cut.

The surgical scissor disposable spray shield 10 can be affirmatively and easily removed from the surgical scissors 16 by holding the surgical scissor disposable spray shield 10 with one hand and, with the other hand, firmly pulling the scissor grips 30a, 30b up and away from the surgical scissor disposable spray shield 10. This motion causes lower arm portion 26a to move above the upper detent 54 allowing the closed sharpened scissor blades 32a, 32b to be pulled easily out of the scissor mount 14.

The surgical scissor disposable spray shield 10 can then be disposed of properly.

An alternative embodiment of the surgical scissor disposable spray shield 10 according to this invention has a shield portion joined to the mount by a flexible attachment member which allows for movement of the shield portion relative to the mount.

From the above disclosure of the general principles of this invention and the preceding detailed description of at least one embodiment, those skilled in the art will readily comprehend the various modifications to which this invention is susceptible. Therefore, I desire to be limited only by the scope of the following claims and equivalents thereof.

I claim:
1. A combination comprising:
 a pair of scissors having a first and a second scissor arm pivotally coupled together at a joint, each scissor arm having a blade portion extending in a first direction from the joint and a handle portion extending in a second direction from the joint, the first and second blade portions being adapted for movement relative to each other in a generally vertical orientation during a cutting action of the pair of scissors, the blade portion of each scissor arm having a tip; and a spray shield having a shield portion, a mount and an opening through which both the first and second scissor arms extend, wherein the spray shield substantially surrounds portions of the first and second scissor arms extending through the opening;

wherein the mount is releasably coupled to the handle portion of the first scissor arm to thereby position the shield portion vertically above the blade portion of the first scissor arm in a covering relationship to deflect and contain a discharge emanating from a member positioned between the first and second blade portions during the cutting action; wherein the mount further comprises: a first and a second detent which are each positioned relative to the handle portion of the first scissor arm to guide movement of the shield portion during the cutting action; wherein the first detent further comprises a first and a second component which are on the first and second mount arms, respectively.

2. The combination of claim 1 wherein a position of the shield portion relative to the blade portion of the first scissor arm is generally constant during the cutting action when the mount is coupled to the handle portion of the first scissor arm.

3. The combination of claim 2 wherein the position of the shield portion relative to the blade portion of the first scissor arm is fixed when the mount is coupled to the handle portion of the first scissor arm.

4. The combination of claim 1 wherein the first and second scissor arms move in a first generally vertical plane proximate the joint during the cutting action, the shield portion supporting the pair of scissors on an underlying surface in an upright generally vertical orientation generally parallel to the first plane when the mount is coupled to the handle portion of the first scissor arm.

5. The combination of claim 4 wherein the shield portion further comprises:

an end cap portion having a terminal edge which rests on the surface to thereby support the pair of scissors in the upright orientation.

6. The combination of claim 1 wherein an end cap portion of the shield portion extends beyond a distal end of the blade portions of the first and second scissor arms.

7. The combination of claim 1 wherein the mount further comprises:

a first and a second mount arm which are positioned on opposite sides of the handle portion of the first scissor arm when the spray shield is mounted to the pair of scissors.

8. The combination of claim 7 wherein the first and second mount arms are adapted to deflect toward and away from each other to releasably mount the spray shield to the pair of scissors and remove the spray shield from the pair of scissors.

9. The combination of claim 1 wherein the mount further comprises:

a first and a second detent which are each positioned relative to the handle portion of the first scissor arm to guide movement of the shield portion during the cutting action.

10. The combination of claim 1 wherein the mount allows for pivotal movement of the first scissor arm relative to the second scissor arm through an arc of up to 90 degrees.

11. The combination of claim 1 wherein the shield portion is closer to the blade portion of the scissor arm to which the shield portion is mounted than to the blade portion of the other scissor arm during the cutting action.

12. A combination comprising:

a pair of scissors having a first and a second scissor arm pivotally coupled together at a joint, each scissor arm having a blade portion extending in a first direction from the joint and a handle portion extending in a second direction from the joint, the first and second blade portions being adapted for movement relative to each other in a generally vertical orientation during a cutting action of the pair of scissors, the blade portion of each scissor arm having a tip;

a spray shield having a shield portion, a mount and an opening through which both the first and second scissor arms extend;

wherein the spray shield substantially surrounds portions of the first and second scissor arms extending through the opening; and wherein the mount is releasably coupled to the handle portion of the first scissor arm to thereby position the shield portion vertically above the blade portion of the scissor arm in a covering relationship to deflect and contain a discharge emanating from a member positioned between the first and second blade portions during the cutting action;

wherein the shield portion is closer to the blade portion of the scissor arm to which the shield portion is mounted than to the blade portion of the other scissor arm during the cutting action;

wherein the mount includes a first and a second mount arm which are positioned on opposite sides of the handle portion of the first scissor arm when the spray shield is mounted to the pair of scissors, the first and second mount arms being adapted to deflect toward and away from each other to releasably mount the spray shield to the pair of scissors and remove the spray shield from the pair of scissors;

wherein the mount includes a first and a second detent which are each positioned relative to the handle portion of the first scissor arm to guide movement of the shield portion during the cutting action;

wherein a position of the shield portion relative to the blade portion of the first scissor arm is generally constant during the cutting action when the mount is coupled to the handle portion of the first scissor arm.

13. The combination of claim 12 wherein the position of the shield portion relative to the blade portion of the first scissor arm is fixed when the mount is coupled to the handle portion of the first scissor arm.

14. The combination of claim 12 wherein the first and second scissor arms move in a first generally vertical plane proximate the joint during the cutting action, the shield portion supporting the pair of scissors on an underlying surface in an upright generally vertical orientation generally parallel to the first plane when the mount is coupled to the handle portion of the first scissor arm.

15. The combination of claim 14 wherein the end cap portion has a terminal edge which rests on the surface to thereby support the pair of scissors in the upright orientation.

16. The combination of claim 12 wherein the first detent further comprises a first and a second component which are on the first and second mount arms, respectively.

17. The combination of claim 12 wherein the mount allows for pivotal movement of the first scissor arm relative to the second scissor arm through an arc of up to 90 degrees.

\* \* \* \* \*